United States Patent
Abdi et al.

(10) Patent No.: US 9,272,261 B2
(45) Date of Patent: Mar. 1, 2016

(54) ORGANIC-INORGANIC HYBRID CHIRAL SORBENT AND PROCESS FOR THE PREPARATION THEREOF

(71) Applicant: Council of Scientific & Industrial Research, New Delhi (IN)

(72) Inventors: Syed Hasan Razi Abdi, Bhavnagar (IN); Rukhsana Ilyas Kureshy, Bhavnagar (IN); Noor-ul Hasan Khan, Bhavnagar (IN); Raksh Vir Jasra, Bhavnagar (IN); Vishal Jitendrabhai Mayani, Bhavnagar (IN); Santosh Agrawal, Bhavnagar (IN)

(73) Assignee: Council of Scientific & Industrial Research, New Delhi (IN)

( * ) Notice: Subject to any disclaimer, the term of this patent is extended or adjusted under 35 U.S.C. 154(b) by 203 days.

(21) Appl. No.: 13/954,402

(22) Filed: Jul. 30, 2013

(65) Prior Publication Data
US 2013/0317244 A1 Nov. 28, 2013

Related U.S. Application Data

(62) Division of application No. 12/443,065, filed as application No. PCT/IN2007/000376 on Aug. 30, 2007, now abandoned.

(30) Foreign Application Priority Data

Sep. 29, 2006 (IN) ............................. 2160/DEL/2006

(51) Int. Cl.
*B01J 20/286* (2006.01)
*B01J 20/28* (2006.01)
*B01J 20/29* (2006.01)
*C07B 57/00* (2006.01)
*B01J 20/32* (2006.01)
*B01J 20/30* (2006.01)
*B01J 20/10* (2006.01)

(52) U.S. Cl.
CPC .............. *B01J 20/286* (2013.01); *B01J 20/103* (2013.01); *B01J 20/28083* (2013.01); *B01J 20/29* (2013.01); *B01J 20/3092* (2013.01); *B01J 20/3204* (2013.01); *B01J 20/3217* (2013.01); *B01J 20/3257* (2013.01); *B01J 20/3259* (2013.01); *B01J 20/3261* (2013.01); *B01J 20/3263* (2013.01); *C07B 57/00* (2013.01); *B01J 2220/54* (2013.01); *B01J 2220/58* (2013.01)

(58) Field of Classification Search
None
See application file for complete search history.

(56) References Cited

PUBLICATIONS

Rocchia et al., Phys. Stat. Sol., (a) 197, No. 2, pp. 365-369 (2003).*

* cited by examiner

*Primary Examiner* — Alicia L Otton
(74) *Attorney, Agent, or Firm* — Fitzpatrick, Cella, Harper & Scinto

(57) ABSTRACT

The present invention provides an organic-inorganic hybrid chiral sorbent for chiral resolution of various racemic compounds viz. racemic mandelic acid, 2-phenyl propionic acid, diethyl tartrate, 2,2'-dihydroxy-1,1'-binaphthalene (BINOL) and cyano chromene oxide with excellent chiral separation (enantiomeric excess, 99%) in case of mandelic acid under medium pressure column chromatography. These optically pure enantiomers find applications as intermediates in pharmaceutical industries.

10 Claims, No Drawings

ORGANIC-INORGANIC HYBRID CHIRAL SORBENT AND PROCESS FOR THE PREPARATION THEREOF

CROSS REFERENCE TO RELATED APPLICATIONS

This application is a divisional of U.S. application Ser. No. 12/443,065, which was the National-Stage of International Application No. PCT/IN2007/000376, filed Aug. 30, 2007, and which is incorporated by reference herein in its entirety.

FIELD OF THE INVENTION

The present invention relates to an organic-inorganic hybrid chiral sorbent. More particularly it relates to optically pure covalently bonded amino alcohol to mesoporous silica as chiral selector for chiral resolution of various racemic compounds, viz. racemic mandelic acid, 2-phenyl propionic acid, diethyl tartrate, 2,2'-dihydroxy-1,1'-binaphthalene (BINOL) and cyano chromene oxide under medium pressure column chromatography. The present invention further relates to a process for the preparation of organic-inorganic hybrid chiral sorbent. These optically pure enantiomers find applications as intermediates in pharmaceutical industries.

BACKGROUND OF THE INVENTION

Resolution of chiral molecules is required in many areas of research. As enzymes and other biological receptor molecules are stereo-specific, enantiomers of a racemic compound may interact with them in a different manner. Consequently, two enantiomers of a racemic compound have different pharmacological activities in many instances. In order to discern these differing effects, the biological activity of each enantiomer needs to be studied separately. This has contributed significantly towards the requirement of enantiomerically pure compounds particularly in pharmaceutical industry and thereby the needs to focus on chiral separation using techniques like chiral chromatography. Various attempts have been made in the past for the development of different stationary phases; for example A. Bielejewska et al. Chem. Anal. (Warsaw) 47 (2002) 419 has reported β-cyclodextrin (β-CD) and permethylated β-cyclodextrin for use of chromatographic separation of mandelic acid and its esters of different aliphatic carbon chain length by reverse phase HPLC. The drawbacks of this process are; (i) β-cyclodextrin alone does not recognize enantiomers of mandelic acid; (ii) stationary phase needs to be permethylated for achieving high chiral separation; (iii) reaction has to be conducted in reverse phase.

S. P. Mendez et al. J. Anal. At. Spectrom. 13 (1998) 893. reported the resolution of D,L-selenomethionine derivatives of OPA (O-phthalaldehyde) and NDA (2,3-naphthalenedicarboxaldehyde) to their respective enantiomers by HPLC on a β-CD chiral column using conventional fluorimetric detection. The drawbacks of this process are; (i) In this study, the amino acid was derivatized using o-phthalaldehyde or naphthalene-2,3-dicarboxaldehyde to allow conventional fluorimetric detection. Such a derivatization step, however, is undesirable because it prolongs the sample preparation time, and requires additional validation because it may be a potential source of contamination, may induce racemization or may complicate the separation.

L. S. Karen et al. Analyst 125 (2000) 281 disclosed the work based on a commercially available HPLC column with a chiral crown ether based stationary phase to perform enantiomeric separations of selenoamino acids without derivatization. The drawbacks of this process are; (i) the need to have dilute perchloric acid as mobile phase for such a column; (ii) The separation of the enantiomers is temperature sensitive.

C. A. L. Ponce de Leon et al. J. Anal. At. Spectrom. 15 (2000) 1103 describes the enantiomeric separation of nine selenoamino acids encountered in selenium-enriched yeast using a crown ether column. The drawbacks of this process are; (i) this reaction involves acidic condition to get effective separation; (ii) The separation process requires lower temperature (18-22° C.) for complete resolution; (iii) the non-polar amino acids may not elute from the column, therefore, a balance between temperature and elution of non-polar compounds is required for an optimum separation.

S. P. Mendez et al. J. Anal. At. Spectrom. 15 (2000) 1109 described the use of teicoplanin-bonded chiral stationary phase (Chirobiotic T) to resolve a variety of underivatized aminoacids. Teicoplanin is a glycopeptide antibiotic which contains 20 chiral centers. The drawbacks of this process are; (i) Teicoplanin is a toxic and naturally occurring complex molecule therefore cannot be easily tuned for various applications (ii) due to the presence of many glycosidic linkages it is prone to hydrolysis and/or alteration in conformation thereby change in optical properties under the elution conditions (iii) this separation process requires pH adjustment about 4 and 7; (iv) separation has to be conducted in reverse phase.

M. Raimondo et al. Chem. Commun. (1997) 1343 used mesoporous silica-based MCM-41 coated on GC capillary columns, as chiral stationary phase to separate different organic molecules The drawbacks of this process are; (i) That separation indeed occurs within the MCM-41 cavities and by a mechanism depending on the proton affinities of the compounds.

M. Grun et al. J. Chromatogr. A 740 (1996) 1 described the behavior of silica, alumina, titania, zirconia and the novel mesoporous aluminosilicate MCM-41 in normal-phase high-performance liquid chromatography under comparable conditions. MCM-41 shows some interesting features as compared to mesoporous crystalline and amorphous oxides. The drawbacks of this process are; (i) This work includes only comparison of an ordered mesoporous aluminosilicate, silica, alumina, titania and zirconia in normal-phase high-performance liquid chromatography; (ii) it requires very large column (250×4 mm).

V. A. Soloshonok, Angew. Chem., Int. Ed. 45 (2006) 766), reported the work based on achiral silica as column packing material for remarkable separation of enantiomers of perfluoroalkyl keto compounds through column chromatography. The drawbacks of this process are; (i) only trifluoromethyl group containing compounds are separated. (ii) variation in results is found with changing the solvents. (iii) In the case of preferential homochiral association, the situation is bit subtle as the formation of dimer will result in different number of enantiomeric (S)(S) and (R)(R) pairs with identical scalar properties. These dimers therefore cannot be separated.

J. H. Kennedy, J. Chromatogr. A 725 (1996) 219 disclosed chiral stationary phases based on polysaccharide derivative coated on silica for chiral separation of different compounds containing carbonyl group and other aromatic ring containing compounds. The drawbacks of this process are; (i) Derivatization of carboxylic acids or eluent modifiers such as acetic acid or diethyl amine is required in this system; (ii) Polysaccharide phases based chiral stationary phase is not predictable and capable of separating both t-acid and n-basic type compounds.

X. Huang et al. Analytical Science 21 (2005) 253 and S. Rogozhin et al. German Patent 1 932 190 (1969); Chem. Abstr., 72 (1970) 90875c have described the use of chiral copper metal complex supported on silica as stationary phase for separation DL-selenomethionine in buffered solution at pH, 5.5 along with methanol as mobile phase. The drawbacks of this process is (i) This separation technique requires 200× 4.6 mm i.d. stainless-steel column; (ii) only underivatized amino acids were resolved on it; (iii) the use of methanol doesn't favor the resolution of DL-selenomethionine; (iv) higher temperature gives some de-activation effect of some biological sample.

J. Bergmann et al. Anal. Bioanal. Chem. 378 (2004) 1624 and M. M. Bayon et al. J. Anal. At. Spectrom. 16(9) (2001) 945 disclosed a fast and sensitive method for the determination of the absolute configuration of Se-amino acids by derivatization process at room temperature by reversed-phase high-performance liquid chromatography-inductively coupled plasma-mass spectrometry. The drawbacks of these process are; (i) separation can be possible in reversed phase HPLC— inductively coupled plasma-mass spectrometry; (ii) Detection limits of about 4 microg L(−1) were obtained; (iii) The derivetization of enantiomers of selenomethionine is necessary. (iv) The final operating conditions involved the use of 50% (v/v) MeOH at pH 5.3 (acetic acid-sodium acetate).

H. Kosugi et al. Chem. Commun. (1997) 1857 described synthesis of (−)-epibatidine and its intermediates by medium pressure liquid chromatography by using achiral silica gel column (Si-10; eluted with 3:1 hexane-EtOAc; UV (254 nm) and RI detectors). The drawbacks of this process are; (i) In this system there is no mechanism of the separation: (ii) It includes only synthesis of (−)-epibatidine and its intermediates; (iii) only hydroxy acetal was separated through achiral column chromatography.

S. P. Mendez et al. J. Anal. At. Spectrom. 14 (1999) 1333 described chiral resolution and speciation of DL-selenomethionine enantiomers by capillary gas chromatography (GC) using an L-valine-tert-butylamide modified polydimethylsiloxane as chiral stationary phase The drawbacks of this process are; (i) good resolution was achieved in the higher temperature range only from 100-160° C.; (ii) requires He as carrier gas; (iii) separation is more difficult for complex biological samples.

R. Vespalec et al. Anal. Chem. 67 (1995) 3223; K. L. Sutton et al. Analyst 125 (2000) 231; S. P. Mendez et al. Anal. Chim. Acta 416 (2000) 1; J. A. Day et al. J. Anal. At. Spectrom. 17 (2002) 27 describes capillary electrophoresis as a tool for the enantiomeric separation selenium containing amino acids, by derivatization process using capillary electrophoresis with UV absorbance detection. The drawbacks of this process are; (i) This separation technique has been used to separate the enantiomers of selenoamino acids by the addition of chiral additives to the electrophoretic buffer; (ii) UV absorbance detection was used in these studies and required the derivatization of the selenoamino acids to permit detection; (iii) UV absorbance detection, without sample pre-concentration, was not sensitive enough to permit the detection of the low levels of selenoamino acids present in complex samples; (iv) applied voltage and pH value gives variation in separation results; (v) buffer system was chosen for good resolution; (vi) addition of methanol to the buffer is required for improved resolution.

B. V. Ernholt et al. Eur. J. Chem. 6 (2000) 278) described the synthesis and enzymatic separation of 1-Azafagomine through achiral regular column chromatography. The drawbacks of this process are; (i) enzymatic separation requires different buffer solutions; (ii) the conversion and enantiomeric excess is affected by varying the solvents, enzymes and its concentration; (iii) low enantiomeric excess was achieved through achiral column chromatography by loading 51% compound.

A. Goswami et al., Z Tetrahedron Asymmetry, 16 (2005) 1715 disclosed enzymatic separation of (±)-sec-butlylamine, lipase and proteases using ether, heptane or dacane as solvent and vinyl butyrate or ethyl butyrate as acylating agent. The drawbacks of this process are; (i) enzymes shows very low enantio-selectivity; (ii) it's a time consuming process (more than 7 days); (iii) solvent, such as acetonitrile, cyclohexane, toluene, methyl-t-butyl ether, 2-methyl-2-pentanol, ethyl caprate is required for this system. Mitsuhashi Kazuya et at in U.S. Pat. No. 278,268 Oct. 23, 2002 disclosed a method for the synthesis of optically active mandelic acid derivatives by enzymatic separation. The drawbacks of this process are; (i) microorganism is essential to generate the (R)-5-mandelic acid derivative or (S)-mandelic acid derivative; (ii) requires appropriate buffer solution.

Mod Takao et al. U.S. Pat. No. 142,914 Oct. 29, 1993 disclosed a process for preparing D-mandelic acid by converting L-mandelic acid into benzoylformic acid followed by stereoselectively reducing it into D-mandelic acid. The drawbacks of this process are; (i) The isolation and collection of microbial cells from culture broth is complicated; (ii) buffer solution is required for maintaining pH; (iii) it is time consuming process.

Endo Takakazu et at in U.S. Pat. No. 677,175 Mar., 29, 1991 disclosed process for producing (R)-(−)-mandelic acid or a derivative through enzymatic separation. The drawbacks of this process are; (i) hydrolysis of mandelonitrile is necessary; (ii) requires neutral or basic reaction system to produce the (R)-(−)-mandelic acid; (iii) requires expensive use of microorganism. and Ghisalba Oreste et at in U.S. Pat. No. 360,802 Jun. 2, 1989 described process for the preparation of R- or S-2-hydroxy-4-phenylbutyric acid in very high enantiomeric purity by enzymatic separation. Disadvantage of this process are; (i) The reduction of the substrate is effected by the so-called final reductase; (ii) suitable as biocatalysts are only purified enzymes; (iii) regeneration of enzyme is complicated.

Hashimoto Yoshihiro et al in U.S. Pat. No. 764,295 Dec. 12, 1996, reported a process for producing an alpha-hydroxy acid or an alpha-hydroxyamide from an aldehyde and prussic acid with a microorganism. The drawbacks of this process are; (i) deactivation of microorganism within a short period of time at higher and lower temperature; (ii) high concentration and high yield is difficult to obtain for alpha-hydroxy acid or alpha-hydroxyamide; (iii) the reaction rate is lowered with an increase in the concentration of the alpha-hydroxy acid or alpha-hydroxyamide product as a result, the reaction does not proceed to completion.

Endo Takakazu et al in U.S. Pat. No. 904,335 Jun. 25, 1992 described a process for producing (R),(S)-mandelic acid or a derivative thereof from mandelonitrile using a microorganism belonging to the genus *Rhodococcus*. The drawbacks of this process are; (i) chiral reagents and microorganism are more expensive; (ii) this method is industrially non-advantageous for producing (R)-(−)-mandelic acid or derivatives; (iii) hydrogenases produced by these bacteria are not always satisfactory.

R. Charles et al. J. Chromatogr. 298 (1984) 516 described the separation of $^{14}$C labelled nicotine through totally achiral column chromatography. The drawbacks of this process are; (i) it requires buffer solution to adjust the pH; (ii) peak-splitting phenomenon was caused by some components of the cation-exchange column or mobile phase.

V. A. Soloshonok et al. J. Fluorine Chemistry, In Press disclosed the self-disproportionation chromatography (SDC) involves the separation of trifluoromethyl group containing compounds and used totally achiral silica as column packing. The drawbacks of this process are; (i) variations in results are found with changing the solvents. (ii) In the case of preferential homochiral association, the situation is bit subtle as the formation of dimmer will result in different number of enantiomeric (S)(S) and (R)(R) pairs with identical scalar properties. These dimers therefore cannot be separated.

OBJECTIVES OF THE INVENTION

The main object of the present invention is to provide an organic-inorganic hybrid chiral sorbent Another object of the invention is to provide a process for the preparation of organic-Inorganic hybrid chiral sorbent.

Yet another object of the present invention is to provide a process for chiral resolution of racemic compounds using optically pure amino alcohols covalently attached on mesoporous silica as chiral selector for chiral resolution of various racemic compounds viz. racemic mandelic acid, 2-phenyl propionic acid, diethyl tartrate, 2,2'-dihydroxy-1,1'-binaphthalene (BINOL) and cyano chromene.

Yet another object of the present invention is to provide chiral resolution of racemic compounds using optically pure amino alcohol covalently attached on mesoporous silica as chiral selector for achieving high Enantiomeric Excess (ee) (99%) at room temperature.

Yet another object of the present invention is to provide chiral resolution of racemic compounds using optically pure amino alcohol covalently attached on mesoporous silica as chiral selector under medium pressure slurry system.

Still another object of the present invention is to provide chiral resolution of racemic compounds using optically pure amino alcohol covalently attached on mesoporous silica as chiral selector under medium pressure (0.5 kp/cm$^2$) column chromatography.

SUMMARY OF THE INVENTION

Accordingly, the present invention provides an organic-inorganic hybrid chiral sorbent comprising amino alcohol covalently bonded to the surface of mesoporous silica material.

In an embodiment of the present invention the amino alcohol used is amino propyl alcohol.

In another embodiment of the present invention the porous silica material used is having porosity in the range of 37 to 100 Å and is selected from the group consisting of MCM-41, SBA-15 and MCF-48.

In yet another embodiment the product obtained in the present invention is represented by the group of following chiral sorbent selected from (S)-aminopropyl alcohol@silica MCM-41, (R)— aminopropyl alcohol@silica MCM-41, (S)-aminopropyl alcohol@silica SBA-15, (R)— aminopropyl alcohol@silica SBA-15, (S)-aminopropyl alcohol@silica MCF-48, (R)— aminopropyl alcohol@ silica MCF-48, (S)—N-methyl aminopropyl alcohol@ silica MCM-41, (R)—N-methyl aminopropyl alcohol@ silica MCM-41, (S)—N,N' dimethyl aminopropyl alcohol@ silica MCM-41, (S)—N,N' dimethyl aminopropyl alcohol@ silica SBA-15 and (S)—N-methyl aminopropyl alcohol@ silica SBA-15.

In yet another embodiment of the invention the chiral sorbent is useful for the separation of racemic mixture of compounds selected from the group consisting of mandelic acid, 2-phenyl propionic acid, diethyl tartrate, 2,2'-dihydroxy-1., 1'-binaphthalene (BINOL) and cyano chromene oxide.

The present invention further provides a process for the preparation of an organic-inorganic hybrid chiral sorbent, the said process comprising the steps of:
 a) silylating the chiral epoxide with a silylating agent in an organic solvent with a molar ratio of chiral epoxide to silylating agent in the range of 1:1 to 1:2.5, in the presence of an inorganic base,
 b) refluxing, the above said mixture obtained in step (a) under an inert atmosphere for a period of 8 to 16 hours, followed by filtration to obtain the resultant filterate,
 c) refluxing, the above said filterate obtained in step (b) with mesoporous silica, under inert atmosphere for a period of about 35 to 55 hours, followed by filtration and washing of the resultant solid product with toluene by known methods,
 d) reacting the resultant washed product obtained in step (c) with aniline or substituted aniline in toluene, under reflux, under an inert atmosphere for a period of 8 to 16 hours, followed by filtration and washing off the resultant product with toluene and extracting the desired chiral sorbent in a solution mixture of toluene and isopropanol by known methods to obtain the desired product of organic-inorganic hybrid chiral sorbent.

In yet another embodiment the chiral epoxide used in step (a) is selected from the group consisting of propene oxide, 1-chloro-2,3-epoxypropane, 1-fluoro-2,3-epoxypropane, 1-bromo-2,3-epoxypropane, 1-methyl-2,3-epoxypropane, 1-methoxy-2,3-epoxypropane and 1-nitro-2,3-epoxypropane.

In yet another embodiment the silylating agent used in step (a) is selected from the group consisting of chloropropyl triethoxysilane, chloropropyltrimethoxy, nitropropyltriethoxysilane, aminopropyltriethoxysilane and aminopropyltrimethoxy silane.

In yet another embodiment the inorganic base used in step (a) is selected from the group consisting of sodium carbonate, potassium carbonate, rubidium carbonate and cesium carbonate.

In yet another embodiment the organic solvent used in step (a) is selected from the group consisting of ethanol, methanol, isopropanol, acetone, acetonitrile, toluene, tetrahydrofuran, dichloroethane and dichloromethane.

In yet another embodiment the mesoporous silica used in step (c) is selected from the group consisting of MCM-41, SBA-15 and MCF-48.

In yet another embodiment the inert atmosphere used is provided by using inert gas selected from nitrogen, argon and helium.

In yet another embodiment the molar amount of aniline or substituted aniline with respect to chiral epoxide is in the range of 1:1 to 1:2.

In yet another embodiment the substituted aniline used is selected from the group consisting of nitroaniline, chloroaniline, methoxyaniline and methylaniline.

In yet another embodiment the amount of mesoporous silica used is in the range of 0.8 to 12 g/mmol of chiral epoxide.

In yet another embodiment the chiral sorbent obtained in step (d) is represented by the group of following sorbents: mandelic acid, 2-phenyl propionic acid, diethyl tartrate, 2,2'-dihydroxy-1,1'-binaphthalene (BINOL) and cyano chromene oxide.

In yet another embodiment the chiral sorbent obtained is useful for the separation of racemic mixtures of compound selected from the group consisting of mandelic acid, 2-phenyl propionic acid, diethyl tartrate, 2,2'-dihydroxy-1,1'-binaphthalene (BINOL) and cyano chromene oxide.

In yet another embodiment the enantiomeric excess of racemates obtained is in the range of 30 to 99%.

In still another embodiment the maximum enantiomeric excess obtained for mandelic acid with aminopropylalcohol@silica sorbent is about 99%.

DESCRIPTION OF THE INVENTION

According to the present invention describes the preparation of organic-inorganic hybrid chiral sorbent, which comprises of
i) silylation of chiral epoxide in the concentration range of 2.557 to 25.57 mmol with aminopropyl triethoxysilane/N-methylaminopropyl triethoxysilane in the concentration range of 2.55 to 25.57 mmol in the presence of $K_2CO_3$/$Na_2CO_3$ in the concentration range of 5.1 to 51 mmol in dry tetrahydrofuran;
ii) refluxing the reaction mixture in the step i) under $N_2$/Ar/He atmosphere in the time range of 8 to 16 h;
iii) filtrating the reaction mixture of step ii) to obtain clear solution;
iv) refluxing the clear solution of step (iii) with mesoporous silica in the range of 2 g to 20 g in dry toluene under $N_2$/Ar/He atmosphere for a period of 35 to 55 h;
v) filtration of reaction mixture of step iv) to obtain solid material, followed by washing with toluene and Soxhlet extraction in toluene;
vi) reacting the washed material obtained in step (v) with aniline/substituted anilines in the concentration range of 5 to 50 mmol under reflux condition in $N_2$/Ar/He atmosphere for a period of 8-16 h in toluene;
vii) filtration of solid sorbent in step vi) followed by washing with toluene, Soxhlet extraction in toluene/isopropanol in the range (9:1 to 7:3) and dried in vacuum;
viii) Taking the chiral column packing material from step vii) in the concentration range of 0.128 to 0.512 mol %
ix) Making slurry of chiral packing material to step viii) by using hexane/isopropanol as column packing solvents in the ratio of (9.5:0.5) to (8:2) and packing in a 260×16 mm glass column;
x) loading of analyte on the packed column from step ix) as solid or dissolving in hexane/isopropanol ratio (1:1) in the concentration range 0.50 to 3.00 mol %;
xi) elution of solvents through column in step x) using hexane/isopropanol in the ratio of (9.5:0.5) to (8:2) using medium-pressure (0.25-0.75 kp/cm$^2$) of nitrogen/argon/helium at room temperature;
xii) collecting the chromatographic fractions (1-12), (13-24) and (25-36) from step xi) in the range of 2 to 6 ml per fraction with an increment of 2 ml after 12 fractions;
xiii) maintaining the medium-pressure (0.25-0.75 kp/cm$^2$) of nitrogen/argon/helium at room temperature through out the step xii)
xiv) examining each collected fractions from step xi to xiii) on an appropriate chiral HPLC column.

In the specification the symbol '@' signifies that the proposed anilino or substituted anilino alcohol is covalently bounded to the surface of the said mesoporous silica material. The symbol '@' should therefore be read as "covalently bonded to the surface of", anywhere in the description.

The synthesis process of amino alcohol modified silica was conducted on laboratory scale in a 100 ml three-necked round bottom flask fitted with an efficient water condenser using S-(+)-epichlorohydrin, 3-aminopropyl triethoxysilane, aniline and silica. The medium pressure column chromatography was carried out by making slurry of (S)-amino alcohol@silica 1 in hexane and isopropanol (9:1) was packed in a 260×16 mm glass column using medium-pressure (0.5 kp/cm$^2$) of nitrogen at room temperature. The analyte solution in isopropanol/hexane (1:1) was loaded on thus packed column that was equilibrated for 1 h. The elution of fractions was done at the pressure mentioned above. Each fraction was subjected to HPLC analysis using an appropriate chiral column. Different analytical grade compounds were used as an analytes. The absolute configuration of different compound was determined by the comparison of HPLC profile with authentic samples.

The separation process according to the present invention was carried out by using amount of analyte in the range of 10 to 30 mg, preferably using 2 g amino alcohol immobilized on silica as column packing material at medium-pressure (0.5 kp/cm$^2$) of nitrogen at room temperature. Higher separation of mandelic acid was obtained when the amount of analyte was more than 10 mg. The chiral products were characterized by the comparison of HPLC profile with authentic samples. In the preferred embodiment, the pressure of the column is maintained (0.25-0.75 kp/cm$^2$) of nitrogen at room temperature. In accordance with the present invention, the chiral amino alcohol immobilized on silica plays a very vital role in achieving better separation of analytes. The amino alcohol used to separate analyte is 2 g. With low quantity of amino alcohol modified silica the separation is sluggish. The use of optimal quantity amino alcohol modified silica (2 g) is essential as it definitely separates the different analyte.

In carrying out the present invention, the time required for the chromatographic separation of analytes is more than 7 h to achieve higher enantiomeric excess. The time of separation may be varied by increasing pressure, it was observed that decreasing the time of chromatographic separation below 5 h resulted in lower separation of analyte The present invention relates to the preparation of chiral compounds suitable for various applications. These chiral compounds were separated from racemic compounds by medium pressure chromatographic separation using amino alcohol as selector at medium-pressure (0.5 kp/cm$^2$) of nitrogen at room temperature. The chromatographic separation of racemic compounds was found to be higher than that reported in literature where the separation depends on i) derivatization of stationary phase as well as analyte, ii) pH of eluents iii) high temperature requirement that result into diffusional problems, reproducibility and difficulty in their reuse. The method of present invention does not require any special device.

The inventive steps adopted in the present invention are:—
(i) generating chirality on inorganic silica surface by covalently binding the simple and readily available chiral organic compounds through silanol groups present on the silica surface.
(ii) Using surface bound chiral amino alcohol as a selector for the chromatographic separation of different compounds at room temperature.
(iii) the resolution of racemic compound is carried out at medium-pressure (0.5 kp/cm$^2$) of nitrogen;

In a typical chromatographic resolution run, the appropriate amino alcohol as selector, hexane/isopropanol as eluents was packed into 260×16 mm glass column using medium-pressure slurry system (0.5 kp/cm$^2$) at room temperature. The analyte solution in isopropanol/hexane (1:1) was loaded on thus packed column that was equilibrated for 1 h. Each fraction was subjected to HPLC analysis using an appropriate chiral column.

The following examples are given by way of illustration of the present invention and therefore should not be construed to limit the scope of the present invention.

EXAMPLE-1

Step 1

(2'S)—N-(2',3'-epoxypropyl)-3-(aminopropyl)-triethoxysilane (S)-(−)-epichlorohydrine (0.2 ml), 3-aminopropyl triethoxy silane (0.598 g), potassium carbonate (0.705 g) and dry tetrahydrofuran were charged in a 3-necked 50 ml round bottom flask equipped with a mechanical stirrer, addition funnel and a reflux condenser connected to a nitrogen inlet. The resulting mixture was stirred at room temperature for 10 minutes and followed by refluxing the mixture for 12 h. The reaction mixture was filtered under an inert atmosphere. Solvent from the filtrate was removed by the dry nitrogen draft: Yield; (0.674 g, 95%).

Step 2

(S)-amino propyl epoxy@silica MCM-41

The product of step 1 (0.674) was dissolved in dry toluene in a 3-necked 50 ml round bottom flask in an inert atmosphere. The dissolved mass was treated with MCM-41 (2.0 g) for 48 h. at the refluxing temperature of toluene. The reaction mass was filtered and washed with dry toluene for several time then dried under vacuum. The dried material was subjected to Soxhlet extraction with dry toluene for 10 h followed by drying the sample under vacuum. Yield; (2 g, loading 22.5% by TGA)

Step 3

(S)-aminopropyl alcohol@silica MCM-41

The epoxy product from the step 2 (22.5% loading, 2 g) was treated with aniline (455 μl) in 10 ml dry toluene in an inert atmosphere. The suspension was refluxed for 12 h. The reaction mixture was cooled to room temperature and the solid was filtered, washed repeatedly with dry toluene and subjected to Soxhlet extraction with toluene and isopropanol (7:3) for 10 h. Finally the sample was dried under vacuum at 40° C. Yield; (2 g, loading 25.6% by TGA).

EXAMPLE-2

Step 1

(2'R)—N-(2',3'-epoxypropyl)-3-(aminopropyl)-triethoxysilane (R)-(−)-epichlorohydrine (0.2 ml), 3-aminopropyl triethoxy silane (0.598 g), potassium carbonate (0.705 g) and dry tetrahydrofuran were reacted and processed in the manner it was done in step 1 of the example 1. Yield (0.680 g, 96%).

Step 2

(R)-aminopropyl epoxy@silica MCM-41

The product of step 1 (0.674) was dissolved in dry toluene in 3-necked 50 ml round bottom flash in an inert atmosphere. Then this dissolved mass was treated with MCM-41 (2.0 g) for 48 h at refluxing temperature. The reaction mixture was processed as per the method given in step 2 of the example 1. (2 g, loading 22M % by TGA)

Step 3

(R)-aminopropyl alcohol@silica MCM-41

The epoxy product from the step 2 (22.0% loading, 2 g) was treated with aniline (455 μl) in 10 ml dry toluene in inert atmosphere. The suspension was treated as per the method given in step 3 of the example 1. Yield (2 g, loading 25.0% by TGA).

EXAMPLE-3

Step 1

(2'S)—N-(2',3'-epoxypropyl)-3-(aminopropyl)-trimethoxysilane (S)-(−)-epibromohydrine (0.2 ml), 3-aminopropyl trimethoxy silane (0.598 g), potassium carbonate (0.705 g) and dry diethyl ether were charged in a 3-necked 50 ml round bottom flask equipped with a mechanical stirrer, addition funnel and a reflux condenser connected to a nitrogen inlet. The resulting mixture was stirred at room temperature for 10 minutes and followed by refluxing the mixture for 10 h. The reaction mixture was filtered under inert atmosphere. Solvent from the filtrate was removed by the dry nitrogen draft. Yield (0.66 g, 95%).

Step 2

(S)-aminopropyl epoxy@silica SBA-15

The product of step 1 (0.65 g) was dissolved in dry toluene in 3-necked 50 ml round bottom flask in an inert atmosphere. Then this dissolved mass was treated with SBA-15 (2.0 g) for 48 h. at refluxing temperature. The reaction mass was filtered and washed with dry toluene for several time then dried under vacuum. The dried material was subjected to Soxhlet extraction with dry toluene for 10 h followed by drying the sample under vacuum. (2.2 g, loading 24.0% by TGA)

Step 3

(S)-aminopropyl alcohol@silica SBA-15

The epoxy product from the step 2 (24.0% loading, 2 g) was treated with aniline (500 μl) in 10 ml dry toluene in an inert atmosphere. The suspension was refluxed for 12 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° c. (2 g, loading 26.5%).

EXAMPLE-4

Step 1

(2'R)—N-(2',3'-epoxypropyl)-3-(aminopropyl)-tributoxysilane (R)-(−)-epichlorohydrine (0.2 ml), 3-aminopropyl tributoxysilane (0.598 g), Sodium carbonate (0.700 g) and dry tetrahydrofuran were charged in a 3-necked 50 ml round bottom flask equipped with a mechanical stirrer, addition funnel and a reflux condenser connected to a nitrogen inlet. The resulting mixture was stirred at room temperature for 10 minutes and followed by refluxing the mixture for 12 h. The reaction mixture was filtered under inert atmosphere. Solvent from the filtrate was removed by the dry nitrogen draft: yield (0.60 g, 94%).

Step 2

(R)-aminopropyl epoxy@silica SBA-15

The product of step 1 (0.674) was dissolved in dry toluene in 3-necked 50 ml round bottom flash in inert atmosphere. Then this dissolved mass was treated with SBA-15 (2.0 g) for 48 h. at refluxing temperature. Reaction was further processed as per the step 2 of the example 3. (2 g, loading 28.0% by TGA).

Step 3

(R)-aminopropyl alcohol@silica SBA-15

The epoxy product from the step 2 (26.0% loading, 2 g) was treated with aniline (500 µl) in 10 ml dry toluene in inert atmosphere. The suspension was refluxed for 12 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 26.2%).

EXAMPLE-5

Step 1

(2'S)—N-(2'3'-epoxypropyl)-3-(aminopropyl)-trimethoxysilane

Synthesized as per the method given in step 1 of the example 1.

Step 2

(S)-aminopropyl epoxy@silica MCF-48

The product of step 1 (0.874 g) was dissolved in dry toluene in 3-necked 50 ml round bottom flask in an inert atmosphere. Then this dissolved mass was treated with MCF-48 (2.0 g) for 48 h. at refluxing temperature. The reaction mass was filtered and washed with dry toluene for several time then dried under vacuum. The dried material was subjected to Soxhlet extraction with dry toluene for 10 h followed by drying the sample under vacuum 2.2 g, loading 27.0% by TGA)

Step 3

(S)-aminopropyl alcohol@ silica MCF-48

The epoxy product from the step 2 (27.0% loading, 2 g) was treated with aniline (600 µl) in 10 ml dry toluene in inert atmosphere. The suspension was refluxed for 12 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 27.6%).

EXAMPLE-6

Step 1

(2'R)—N-(2',3'-epoxypropyl)-3-(aminopropyl)-trimethoxysilane

This material was synthesized as per the method described in step 1 of the example 1.

Step 2

(R)-aminopropyl epoxy@ silica MCF-48

The product of step 1 (0.674 g) was dissolved in dry toluene in 3-necked 50 ml round bottom flash in inert atmosphere. Then this dissolved mass was treated with MCF-48 (2.0 g) and processed as per the method of step 2 of example 5. Yield; 2 g, loading 26.5% by TGA.

Step 3

(R)-aminopropyl alcohol@ silica MCF-48

The epoxy product from the step 2 (26.5% loading, 2 g) was treated with aniline (600 µl) in 10 ml dry toluene in an inert atmosphere and the reaction was processed as per the step 3 of the example 5. (Yield; 2 g, loading 27.0%).

EXAMPLE-7

Step 1

(2'S)—N'-(2',3'-epoxypropyl)-3-(N-methylaminopropyl)-trimethoxysilane (S)-(−)-epichlorohydrine (0.2 ml), 3-N-methylaminopropyl trimethoxy silane (0.700 g), potassium carbonate (0.705 g) and dry toluene were charged in a 3-necked 50 ml round bottom flask equipped with a mechanical stirrer, addition funnel and a reflux condenser connected to a nitrogen inlet. The resulting mixture was stirred at RT for 10 minutes and followed by refluxing the mixture for 16 h. The reaction mixture was filtered under inert atmosphere. Solvent from the filtrate was removed by the dry nitrogen draft: yield (0.715 g, 96%).

Step 2

(S)—N-methyl aminopropyl epoxy@silica MCM-41

The product of step 1 (0.700 g) was dissolved in dry toluene in 3-necked 50 ml round bottom flask in an inert atmosphere. The reaction mixture was treated with MCM-41 (2 g) for 48 h. at the refluxing temperature of toluene. The reaction mass was filtered and washed with dry toluene for several time then dried under vacuum. The dried material was subjected to Soxhlet extraction with dry toluene for 10 h followed by drying the sample under vacuum (2.2 g, loading 20.5% by TGA)

Step 3

(S)—N-methyl aminopropyl alcohol@silica SBA-41

The epoxy product from the step 2 (20.5% loading, 2 g) was treated with aniline (455 μl) in 10 ml dry toluene in an inert atmosphere. The suspension was refluxed for 12 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 25.6%).

EXAMPLE-8

Step 1

(2'R)—N'-(2',3'-epoxypropyl)-3-(N-methylaminoaminopropyl)-trimethoxysilane (R)-(−)-epichlorohydrine (0.2 ml), 3-N-methylaminopropyl trimethoxy silane (0.598 g), sodium carbonate (0.705 g) and dry methanol were charged in a 3-necked 50 ml round bottom flask equipped with a mechanical stirrer, addition funnel and a reflux condenser connected to a nitrogen inlet. The reaction was processed as per the method given in step 1 of the example 7. Yield (0.725 g, 97%).

Step 2

(R)—N-methyl aminopropyl epoxy@silica MCM-41

The product of step 1 (0.700 g) was dissolved in dry toluene in 3-necked 50 ml round bottom flask in inert atmosphere. Then this dissolved mass was treated with MCM-41 (2.0 g) in the manner described in step 2 of the example 7. (2.0 g, loading 21.0% by TGA)

Step 3

(R)—N-methyl aminopropyl alcohol@silica MCM-41

The epoxy product from the step 2 (21.1% loading, 2 g) was treated with aniline (455 μl) in 10 ml dry toluene in an inert atmosphere. The reaction was processed as per the method described in step 3 of the example 7. Yield (2 g, loading 25.0%).

EXAMPLE-9

Step 1

(2'S)—N'-(2',3'-epoxypropyl)-3-(N-methylaminopropyl)-trimethoxysilane

This material was synthesized by following the method given in step 1 of the example 7.

Step 2

(S)—N-methyl aminopropyl epoxy@silica SBA-15

The product of step 1 (0.674 g) was dissolved in dry toluene in 3-necked 50 ml round bottom flask in an inert atmosphere. Then this dissolved mass was treated with SBA-15 (2.0 g) for 48 h. at refluxing temperature. The reaction mass was filtered and washed with dry toluene for several time then dried under vacuum. The dried material was subjected to Soxhlet extraction with dry toluene for 10 h followed by drying the sample under vacuum. Yield (2.4 g, loading 23.5% by TGA).

Step 3

(S)—N-methyl aminopropyl alcohol@silica SBA-15

The epoxy product from the step 2 (23.5% loading, 2 g) was treated with aniline (600 μl) in 10 ml dry toluene in an inert atmosphere. The suspension was refluxed for 12 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 26.8%).

EXAMPLE-10

Step 1

(2'S)—N'-(2',3'-epoxypropyl)-3-(N-methylaminopropyl)-trimethoxysilane

This material was prepared by the method described in the step 1 of the example 7.

Step 2

(S)—N-methyl aminopropyl epoxy@silica MSM-41 this material was prepared by following the procedure given in step 2 of the example 7.

Step 3

(S)—N,N' dimethyl aminopropyl alcohol@silica MCM-41

The epoxy product from the step 2 (20.5% loading, 2 g) was treated with N-methylaniline (600 μl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-11

Step 1

(2'S)—N'-(2',3'-epoxypropyl)-3-(N-methylaminopropyl)-trimethoxysilane

This material was prepared by the method described in the step 1 of the example 7.

Step 2

(S)—N-methyl aminopropyl epoxy@silica MCM-41

This material was prepared by following the procedure given in step 2 of the example 7.

Step 3

(S)—N-methyl aminopropyl alcohol@silica MCM-41

The epoxy product from the step 2 (20.5% loading, 2 g) was treated with 4-methyl aniline (600 µl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-12

Step 1

(2'S)—N'-(2',3'-epoxypropyl)-3-(N-methylaminopropyl)trimethoxysilane

This material was prepared by the method described in the step 1 of the example 7.

Step 2

(S)—N-methyl aminopropyl epoxy@silica MCM-41

This material was prepared by following the procedure given in step 2 of the example 7.

Step 3

(S)—N-methyl aminopropyl alcohol@silica MCM-41

The epoxy product from the step 2 (20.5% loading, 2 g) was treated with 4-chloro aniline (600 µl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-13

Step 1

(2'S)—N'-(2',3'-epoxypropyl)-3-(N-methylaminopropyl)-trimethoxysilane

This material was prepared by the method described in the step 1 of the example 7.

Step 2

(S)—N-methyl aminopropyl epoxy@silica

This material was prepared by following the procedure given in step 2 of the example 7.

Step 3

(S)—N-methyl aminopropyl alcohol@silica-MCM-41

The epoxy product from the step 2 (20.5% loading, 2 g) was treated with 4-methoxy aniline (600 µl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-14

Step 1

(2'S)—N'-(2',3'-epoxypropyl)-3-(N-methylaminopropyl)-trimethoxysilane

This material was prepared by the method described in the step 1 of the example 5.

Step 2

(S)-aminopropyl epoxy@ silica MCF-48 this material was prepared by following the procedure given in step 2 of the example 5.

Step 3

(S)-aminopropyl alcohol@ silica MCF-48

The epoxy product from the step 2 (20.5% loading, 2 g) was treated with 4-methoxy aniline (600 µl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-15

Step 1

(2'S)—N'-(2',3'-epoxypropyl)-3-(N-methylaminopropyl)-trimethoxysilane

This material was prepared by the method described in the step 1 of the example 5.

Step 2

(S)-aminopropyl epoxy@ silica MCF-48 this material was prepared by following the procedure given in step 2 of the example 5.

Step 3

(S)-aminopropyl alcohol@ silica MCF-48

The epoxy product from the step 2 (20.5% loading, 2 g) was treated with 4-chloro aniline (600 µl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-16

Step 1

(2'S)—N'-(2',3'-epoxypropyl)-3-(N-methylaminopropyl)-trimethoxysilane

This material was prepared by the method described in the step 1 of the example 5.

Step 2

(S)-aminopropyl epoxy@ silica MCF-48 this material was prepared by following the procedure given in step 2 of the example 5.

Step 3

(S)-aminopropyl alcohol@ silica MCF-48

The epoxy product from the step 2 (20.5% loading. 2 g) was treated with 4-methyl aniline (600 μl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-17

Step 1

(2'S)—N'-(2',3'-epoxypropyl)-3-(N-methylaminopropyl)-trimethoxysilane

This material was prepared by the method described in the step 1 of the example 9.

Step 2

(S)—N-methylaminopropyl epoxy@silica SBA-15

This material was prepared by following the procedure given in step 2 of the example 9.

Step 3

(S)—N,N'-dimethyl aminopropyl alcohol@silica SBA-15

The epoxy product from the step 2 (20.5% loading, 2 g) was treated with 4-methyl aniline (600 μl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23:5%).

EXAMPLE-18

Step 1

(2'S)—N'-(2',3'-epoxypropyl)-3-(N-methylaminopropyl)-trimethoxysilane

This material was prepared by the method described in the step 1 of the example 9.

Step 2

(S)—N-methyl aminopropyl epoxy@silica SBA-15

This material was prepared by following the procedure given in step 2 of the example 9.

Step 3

(S)—N-methyl aminopropyl alcohol@silica SBA-15

The epoxy product from the step 2 (20.5% loading, 2 g) was treated with 4-methoxy aniline (600 μl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-19

Step 1

(2'S)—N'-(2',3'-epoxypropyl)-3-(N-methylaminopropyl)-trimethoxysilane

This material was prepared by the method described in the step 1 of the example 9.

Step 2

(S)—N-methylaminopropyl epoxy@silica SBA-15

This material was prepared by following the procedure given in step 2 of the example 9.

Step 3

(S)—N-methyl aminopropyl alcohol@silica SBA-15

The epoxy product from the step 2 (20.5% loading, 2 g) was treated with 4-chloro aniline (600 μl) in 10 ml dry toluene in an inert atmosphere. The suspension was refluxed for 18 h. The reaction mixture was cooled to room temperature and the solid was filtered, washed repeatedly with dry toluene and subjected to the soxhlet extraction with toluene and isopropanol (7:3) for 10 h. Finally the sample was dried under vacuum at 40° C. (2 g, loading 23.5%).

EXAMPLE-20

Step 1

(2'S)—N-(2',3'-epoxypropyl)-3-(aminopropyl)-triethoxysilane (S)-(−)-Ephedrine (0.2 ml), 3-aminopropyl triethoxy silane (0.598 g), potassium carbonate (0.705 g) and dry tetrahydrofuran were charged in a 3-necked 50 ml round bottom flask equipped with a mechanical stirrer, addition funnel and a reflux condenser connected to a nitrogen inlet. The resulting mixture was stirred at RT for 10 minutes and followed by refluxing the mixture for 12 h. The reaction mixture was filtered under an inert atmosphere. Solvent from the filtrate was removed by the dry nitrogen draft: Yield; (0.674 g, 95%).

Step 2

(S)-aminopropyl epoxy@silica MCM-41

The product of step 1 (0.674) was dissolved in dry toluene in a 3-necked 50 ml round bottom flask in an inert atmosphere. The dissolved mass was treated with MCM-41 (2.0 g) for 48 h. at the refluxing temperature of toluene. The reaction mass was filtered and washed with dry toluene for several time then dried under vacuum. The dried material was subjected to Soxhlet extraction with dry toluene for 10 h followed by drying the sample under vacuum. Yield; (2 g, loading 22.5% by TGA)

Step 3

(S)-aminopropyl alcohol@silica MCM-41

The epoxy product from the step 2 (22.5% loading, 2 g) was treated with aniline (455 µl) in 10 ml dry toluene in an inert atmosphere. The suspension was refluxed for 12 h. The reaction mixture was cooled to room temperature and the solid was filtered, washed repeatedly with dry toluene and subjected to Soxhlet extraction with toluene and isopropanol (7:3) for 10 h. Finally the sample was dried under vacuum at 40° c. Yield; (2 g, loading 25.6% by TGA).

EXAMPLE-21

Step 1

(2'S)—N-(2',3'-epoxypropyl)-3-(aminopropyl)-triethoxysilane (S)-(−)-PsaudoEphedrine (0.2 ml), 3-chloro propyl triethoxy silane (0.598 g), potassium carbonate (0.705 g) and dry tetrahydrofuran were charged in a 3-necked 50 ml round bottom flask equipped with a mechanical stirrer, addition funnel and a reflux condenser connected to a nitrogen inlet. The resulting mixture was stirred at RT for 10 minutes and followed by refluxing the mixture for 12 h. The reaction mixture was filtered under an inert atmosphere. Solvent from the filtrate was removed by the dry nitrogen draft: Yield; (0.674 g, 95%).

Step 2

(S)-aminopropyl epoxy@silica MCM-41

The product of step 1 (0.674) was dissolved in dry toluene in a 3-necked 50 ml round bottom flask in an Inert atmosphere. The dissolved mass was treated with MCM-41 (2.0 g) for 48 h. at the refluxing temperature of toluene. The reaction mass was filtered and washed with dry toluene for several time then dried under vacuum. The dried material was subjected to Soxhlet extraction with dry toluene for 10 h followed by drying the sample under vacuum. Yield; (2 g, loading 22.5% by TGA)

Step 3

(S)-aminopropyl alcohol@silica MCM-41

The epoxy product from the step 2 (22.5% loading, 2 g) was treated with aniline (455 µl) in 10 ml dry toluene in an inert atmosphere. The suspension was refluxed for 12 h. The reaction mixture was cooled to room temperature and the solid was filtered, washed repeatedly with dry toluene and subjected to Soxhlet extraction with toluene and isopropanol (7:3) for 10 h. Finally the sample was dried under vacuum at 40° C. Yield; (2 g, loading 25.6% by TGA).

EXAMPLE-22

In a medium pressure chromatographic column, slurry of (S)-aminopropyl alcohol@silica 1 (0.128 mol %) in hexane and isopropanol (9:1) was packed in a 260×16 mm glass column using medium-pressure (0.5 kp/cm$^2$) of nitrogen at room temperature. The solid racemic mandelic acid (3.00 mol %) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess of mandelic acid found 7.4%.

EXAMPLE-23

To a medium pressure chromatographic column, slurry of (S)-aminopropyl alcohol@silica 1 (0.128 mol %) in hexane and isopropanol (9:1) was packed in a 260×16 mm glass column using medium-pressure (0.5 kp/cm$^2$) of nitrogen at room temperature. The solid racemic mandelic acid (3.00 mol %) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess, enantiomeric excess of mandelic acid found 7.4%.

EXAMPLE-24

To a medium pressure chromatographic column, slurry of (S)-aminopropyl alcohol@silica 1 (0.512 mol %) in hexane and isopropanol (9:1) was packed in a 260×16 mm glass column using medium-pressure (0.5 kp/cm$^2$) of nitrogen at room temperature. The solid racemic mandelic acid (1.50 mol %) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess of mandelic acid found 8.3%.

EXAMPLE-25

To a medium pressure chromatographic column, slurry of (S)-aminopropyl alcohol@silica 1 (0.512 mol %) in hexane and isopropanol (9:1) was packed in a 260×16 mm glass column using medium-pressure (0.5 kp/cm$^2$) of nitrogen at room temperature. The racemic mandelic acid (1.50 mol %) dissolved in isopropanol/hexane (1:1) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess of mandelic acid found 99.4%.

EXAMPLE-26

To a medium pressure chromatographic column, slurry of (S)-aminopropyl alcohol@silica 1 (0.486 mol %) in hexane and isopropanol (9:1) was packed in a 260×16 mm glass column using medium-pressure (0.5 kp/cm$^2$) of nitrogen at room temperature. The racemic mandelic acid (1.58 mol %) dissolved in isopropanol/hexane (1:1) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess of mandelic acid found 99.0%.

EXAMPLE-27

To a medium pressure chromatographic column, slurry of (S)-aminopropyl alcohol@silica 1 (0.479 mol %) in hexane and isopropanol (9:1) was packed in a 260×16 mm glass column using medium-pressure (0.5 kp/cm$^2$) of nitrogen at room temperature. The racemic mandelic acid (1.60 mol %) dissolved in isopropanol/hexane (1:1) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess of mandelic acid found 98.8%.

EXAMPLE-28

To a medium pressure chromatographic column, slurry of (S)-aminopropyl alcohol@silica 1 (0.512 mol %) in hexane and isopropanol (9:1) was packed in a 260×16 mm glass column using medium-pressure (0.5 kp/cm$^2$) of nitrogen at room temperature. The racemic mandelic acid (0.50 mol %) dissolved in isopropanol/hexane (1:1) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. The enantiomeric excess, enantiomeric excess of mandelic acid found 98.5%

EXAMPLE-29

To a medium pressure chromatographic column, slurry of MCM-41 (0.512 mol %) in hexane and isopropanol (9:1) was packed in a 260×16 mm glass column using medium-pressure (0.5 kp/cm$^2$) of nitrogen at room temperature. The racemic mandelic acid (0.50 mol %) dissolved in isopropanol/hexane (1:1) was loaded on thus packed column that was equilibrated for 1 h. The elution of fractions was done at the pressure mentioned above. Each fraction was subjected to HPLC analysis using an appropriate Chiralcel OD column, eluent hexane/isopropanol (9:1) at 220 nm. No separation of mandelic acid was found.

EXAMPLE-30

To a medium pressure chromatographic column, slurry of (S)-aminopropyl alcohol@silica 1 (0.512 mol %) in hexane and isopropanol (8:2) was packed in a 260×16 mm glass column using medium-pressure (0.5 kp/cm$^2$) of nitrogen at room temperature. The racemic 2,2'-dihydroxy-1,1'-binaphthalene (BINOL) (0.50 mol %) dissolved in isopropanol/hexane (1:1) was loaded on packed column that was equilibrated for 1 h. The elution of fractions was done at the pressure mentioned above. Each fraction was subjected to HPLC analysis using an appropriate Chiralpak AD column, eluent hexane/isopropanol (8:2) at 254 nm. The enantiomeric excess, enantiomeric excess of 2,2'-dihydroxy-1,1'-binaphthalene (BINOL) found 19.5%.

EXAMPLE-31

To a medium pressure chromatographic column, slurry of (S)-aminopropyl alcohol@silica 1 (0.512 mol %) in hexane and isopropanol (9:1) was packed in a 260×16 mm glass column using medium-pressure (0.5 kp/cm$^2$) of nitrogen at room temperature. The racemic cyanochromene oxide (CNCR) (0.50 mol %) dissolved in isopropanol/hexane (1:1) was loaded on packed column that was equilibrated for 1 h. The elution of fractions was done at the pressure mentioned above. Each fraction was subjected to HPLC analysis using an appropriate Chiralcel OD column, eluent hexane/isopropanol (9:1) at 254 nm. The enantiomeric excess cyanochromene oxide (CNCR) of found 3.8%.

EXAMPLE-32

To a medium pressure chromatographic column, slurry of (S)-aminopropyl alcohol@silica 1 (0.512 mol %) in hexane and isopropanol (8:2) was packed in a 260×16 mm glass column using medium-pressure (0.5 kp/cm$^2$) of nitrogen at room temperature. The solution of racemic diethyl-tartrate (0.50 mol %) in isopropanol/hexane (1:1) was loaded on packed column that was equilibrated for 1 h. The elution of fractions was done at the pressure mentioned above. Each fraction was subjected to HPLC analysis using an appropriate Chiralpak AD column, eluent hexane/isopropanol (8:2) at 220 nm. The enantiomeric excess of diethyl-tartrate found 11.5%.

EXAMPLE-33

To a medium pressure chromatographic column, slurry of (S)-aminopropyl alcohol@silica 1 (0.512 mol %) in hexane and isopropanol (9.5:0.5) was packed in a 260×16 mm glass column using medium-pressure (0.5 kp/cm$^2$) of nitrogen at room temperature. The solution of racemic 2-phenyl propionic acid (0.50 mol %) in isopropanol/hexane (1:1) was loaded on thus packed column that was equilibrated for 1 h. The elution of fractions was done at the pressure mentioned above. Each fraction was subjected to HPLC analysis using an appropriate Chiralcel OD column, eluent hexane/isopropanol/formic acid (9:8.1) at 254 nm. The enantiomeric excess of 2-phenyl propionic acid found 33.5%

EXAMPLE-34

The same procedure as exemplified in example 1 was repeated with various racemic compounds viz., 2-phenyl propionic acid, diethyl tartrate, 2,2'-dihydroxy-1,1'-binaphthalene (BINOL) and cyano chromene oxide under medium pressure column chromatography. The results are summarized in Table 1 and 2.

TABLE 1

Separation of Mandelic acid varying amount of Mandelic acid and packing material

| Entry | Amount of Mandelic acid m·mol | Column Packing Material[c] 1(g) | Loading of Mandelic acid[e] (%) | Eluent[f] | % ee max[g] | Absolute configuration |
|---|---|---|---|---|---|---|
| 1 | 0.099[a] | 0.50 | 3.0 | Hex/IPA = 9:1 | 7.4 | R |
| 2 | 0.197[a] | 2.00 | 1.5 | Hex/IPA = 9:1 | 8.3 | R |
| 3 | 0.197[b] | 2.00 | 1.5 | Hex/IPA = 9:1 | 99.4 | R |
| 4 | 0.197[b] | 1.90 | 1.5 | Hex/IPA = 9:1 | 99.0 | R |
| 5 | 0.197[b] | 1.87 | 1.5 | Hex/IPA = 9:1 | 98.8 | R |
| 6 | 0.066[b] | 2.00 | 0.5 | Hex/IPA = 9:1 | 98.5 | R |
| 7 | 0.066[b] | MCM-41[d] | 0.5 | Hex/IPA = 9:1 | — | R + S (50:50%) |

[a]Mandelic acid loaded on column as solid,
[b]Mandelic acid loaded on column after dissolving in Isopropanol/Hexane,
[c](S)-amino propyl alcohol@silica is used as column packing material
[d]MCM-41 is used as column packing material (2 gm),
[e]percentage loading of mandelic acid according to column packing material,
[f]Hex = hexane, IPA = isopropanol,
[g]Enantiomeric Excess of R-mandelic acid using HPLC chiralcel OD column, eluent Hexane/IPA = 9:1 at 220 nm.,
[h]absolute configuration were determined by the comparison of HPLC profile with authentic samples.

TABLE 2

Data for separation of different compounds by flash column chromatography[a]

| Entry | Name of compound (racemic) | Sample amount[f] (mg) | Column Packing Material 1 (g) | Eluent[g] | % ee max | Absolute configuration[h] |
|---|---|---|---|---|---|---|
| 8 | BINOL[b] | 10 | 2.0 | Hex/IPA = 8:2 | 19.5 | R |
| 9 | CNCR[c] | 10 | 2.0 | Hex/IPA = 9:1 | 3.8 | 3S, 4S |
| 10 | Diethyl Tartrate[d] | 10 | 2.0 | Hex/IPA = 8:2 | 11.5 | 2R, 3R |
| 11 | 2-phenyl Propionic acid[e] | 10 | 2.0 | Hex/IPA = 9.5:0.5 | 33.5 | S |

[a]All the experiments were conducted under the same condition unless otherwise stated. Temperature (27° C.), amount of sample m = 0.0100 ± 0.0001 g, column diameter d = 16 mm, length = 260 mm, Enantiomeric excess was determined by HPLC analysis by mentioned columns. (l = 25 cm, d = 0.46 cm).
[b]Chiralpak AD column, eluent Hexane/IPA = 8:2 at 254 nm.
[c]Cyanochromene oxide(CNCR) chiralcel OD column, eluent Hexane/IPA = 9:1 at 254 nm.
[d]Chiralpak AD column, eluent Hexane/IPA = 9:1 at 220 nm.
[e]Chiralcel OD column, eluent Hexane/IPA/Formic acid = 98:2:1 at 254 nm.
[f]Analyte loaded on column after dissolving in Isopropanol/Hexane.
[g]Hex = hexane, IPA = isopropanol.
[h]The absolute configuration were determined by the comparison of HPLC profile with authentic samples.

ADVANTAGES OF THE INVENTION

Resolution of different compounds is achievable with inexpensive medium pressure column chromatography.

Organic selector based amino alcohol modified silica (2 g) is sufficient enough for the separation of enantiomers in the present invention at room temperature.)

Only smaller quantity of column packing material is required to carry out for the repeated experiments using medium pressure column chromatography.

Organic solvents like hexane and isopropanol are used as column packing solvents as well as eluents.)

Under the defined chromatographic conditions the resolution of enantiomers is carried out by medium-pressure range from (0.25-0.75 kp/cm$^2$) of nitrogen at room temperature.

Separation chromatography is carried out in air and no prior oxygen free conditions are required.

A simple glass column is required for packing purpose.

Using the present invention high resolution of racemates having excellent enantiomeric excess was achieved within reasonable time period that makes the process viable for industrial application.

By carrying out the Soxhlet extraction process, the amino alcohol modified silica can be reused for repeated experiments.

The invention claimed is:

1. A process for preparation of an organic-inorganic hybrid chiral sorbent comprising N-methylaminopropyl or aminopropyl alcohol covalently bonded to a surface of a mesoporous silica material, the process comprising the steps of:
   (a) silylating a chiral epoxide with 3-aminopropyltriethoxysilane or 3-N-methyl aminopropyltrimethoxysilane in an organic solvent with a molar ratio of the chiral epoxide to the 3-aminopropyltriethoxysilane or 3-N-methyl aminopropyltrimethoxysilane of 1:1 to 1:2.5 in the presence of an inorganic base to form a reaction mixture;
   (b) refluxing the reaction mixture obtained in the step (a) under an inert atmosphere for a period of 8 to 16 hours, followed by filtration to obtain a resultant filtrate;
   (c) refluxing the resultant filtrate obtained in the step (b) with the mesoporous silica, under an inert atmosphere for a period of 35 to 55 hours, followed by filtration and washing of a resultant solid product with toluene to obtain a resultant washed product; and
   (d) reacting the resultant washed product obtained in the step (c) with aniline or substituted aniline in toluene, under reflux, under an inert atmosphere for a period of 8 to 16 hours, followed by filtration and washing of a resultant product with toluene and extracting the chiral sorbent in a solution mixture of toluene and isopropanol to obtain the organic-inorganic hybrid chiral sorbent.

2. The process according to claim 1, wherein the chiral epoxide in the step (a) is selected from the group consisting of propene oxide, 1-chloro-2,3-epoxypropane, 1-fluoro-2,3-epoxypropane, 1-bromo-2,3-epoxypropane, 1-methyl-2,3-epoxypropane, 1-methoxy-2,3-epoxypropane, and 1-nitro-2,3-epoxypropane.

3. The process according to claim 1, wherein the inorganic base in the step (a) is selected from the group consisting of sodium carbonate, potassium carbonate, rubidium carbonate, and cesium carbonate.

4. The process according to claim 1, wherein the organic solvent in the step (a) is selected from the group consisting of ethanol, methanol, isopropanol, acetone, acetonitrile, toluene, tetrahydrofuran, dichloroethane, and dichloromethane.

5. The process according to claim 1, wherein the mesoporous silica in the step (c) is selected from the group consisting of MCM-41, SBA-15, and MCF-48.

6. The process according to claim 1, wherein the inert atmosphere in the steps (b) to (d) is provided by using an inert gas selected from the group consisting of nitrogen, argon, and helium.

7. The process according to claim 1, wherein a molar amount of the aniline or substituted aniline with respect to the chiral epoxide is from 1:1 to 1:2.

8. The process according to claim 1, wherein the substituted aniline is selected from the group consisting of nitroaniline, chloroaniline, methoxyaniline, and methylaniline.

9. The process according to claim 1, wherein an amount of the mesoporous silica is from 0.8 to 12 g/mmol of the chiral epoxide.

10. A process of separating a racemic mixture of a compound selected from the group consisting of mandelic acid, 2-phenyl propionic acid, diethyl tartrate, 2,2'-dihydroxy-1,1'-binaphthalene (BINOL), and cyano chromene oxide, comprising contacting the racemic mixture with an organic-inorganic hybrid chiral sorbent obtained by the process according to claim 1.

* * * * *